(12) United States Patent  (10) Patent No.: US 8,682,432 B2
Nakajima  (45) Date of Patent: Mar. 25, 2014

(54) CARDIAC-EVENT PROCESSOR AND HEART TREATMENT DEVICE

(75) Inventor: Keiichiro Nakajima, Tokyo (JP)

(73) Assignee: Olympus Corporation, Tokyo (JP)

( * ) Notice: Subject to any disclaimer, the term of this patent is extended or adjusted under 35 U.S.C. 154(b) by 468 days.

(21) Appl. No.: 12/884,932

(22) Filed: Sep. 17, 2010

(65) Prior Publication Data

US 2011/0106198 A1    May 5, 2011

(30) Foreign Application Priority Data

Oct. 30, 2009 (JP) ................................. 2009-250442
Oct. 30, 2009 (JP) ................................. 2009-250443

(51) Int. Cl.
*A61N 1/08* (2006.01)
(52) U.S. Cl.
USPC ............................................ 607/17; 600/510
(58) Field of Classification Search
USPC ..................................... 607/17; 600/510, 523
See application file for complete search history.

(56) References Cited

U.S. PATENT DOCUMENTS

| 5,203,326 | A | * | 4/1993 | Collins | 607/4 |
| 5,916,239 | A | * | 6/1999 | Geddes et al. | 607/14 |
| 5,948,005 | A | | 9/1999 | Valikai et al. | |
| 6,941,167 | B2 | | 9/2005 | Stahmann et al. | |
| 7,783,353 | B2 | * | 8/2010 | Libbus et al. | 607/18 |

FOREIGN PATENT DOCUMENTS

| JP | 02-291873 | 12/1990 |
| JP | Hei 8-38625 | 2/1996 |
| JP | 2004-173790 | 6/2004 |
| JP | 2004-275427 A | 10/2004 |
| JP | 2005-013504 A | 1/2005 |
| WO | WO-86-05698 | 10/1986 |
| WO | WO 01/26729 A1 | 4/2001 |
| WO | WO-2006-055849 A1 | 5/2006 |
| WO | WO-2006-099038 A1 | 9/2006 |
| WO | WO-2008-045598 A1 | 4/2008 |
| WO | WO-2008-143814 A2 | 11/2008 |

* cited by examiner

*Primary Examiner* — Tammie K Heller
(74) *Attorney, Agent, or Firm* — Scully, Scott, Murphy & Presser, P.C.

(57) ABSTRACT

Provided is a cardiac-event processor (1) including a storing unit (11) that stores a time history of cardiac events, including heartbeats, in association with the presence/absence of nerve stimulation; a heart rate calculator (12) that calculates a heart rate for when each heartbeat is detected, on the basis of the time history of the cardiac events stored in the storing unit (11); and a frequency data generator (13) that separately adds up frequencies of the heart rates calculated by the heart rate calculator (12) for the cases with and without the nerve stimulation.

7 Claims, 12 Drawing Sheets

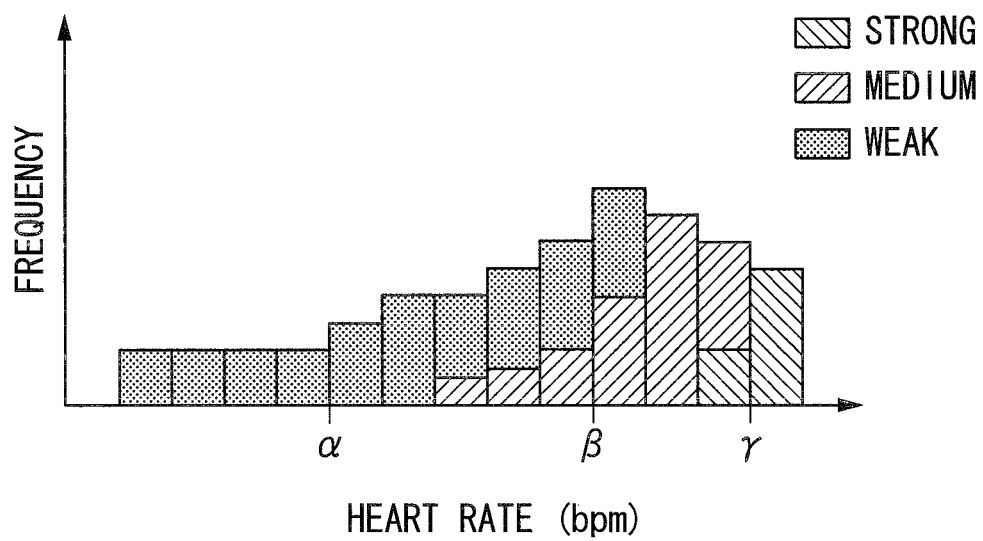

140 # CARDIAC-EVENT PROCESSOR AND HEART TREATMENT DEVICE

BACKGROUND OF THE INVENTION

1. Field of the Invention

The present invention relates to a cardiac-event processor and a heart treatment device.

This application is based on Japanese Patent Application Nos. 2009-250442 and 2009-250443, the contents of which are incorporated herein by reference.

2. Description of Related Art

Conventionally, a heart treatment device that treats tachycardia or fibrillation by reducing the heart rate with electrical stimulation of the vagus nerve has been known (for example, see Japanese Unexamined Patent Application, Publication No. 2004-173790 and Japanese Unexamined Patent Application, Publication No. Hei 8-38625). On the other hand, a device and a method wherein information on cardiac events is stored in an implantable medical device, the stored information is acquired by external equipment, and the state of a heart is displayed as a histogram have been known (for example, see U.S. Pat. No. 6,941,167 Specification). A doctor diagnoses the state of the heart of a patient and considers treatment methods, using the displayed histogram.

With the device disclosed in U.S. Pat. No. 6,941,167, heart treatment by nerve stimulation is not taken into consideration. Therefore, when a patient has an implanted heart treatment device, which enables nerve stimulation, cardiac-event information acquired from the patient is displayed as a single histogram without distinguishing unstimulated heartbeats of the patient from the heartbeats due to the nerve stimulation.

BRIEF SUMMARY OF THE INVENTION

An object of the present invention is to provide a cardiac-event processor that is capable of accurately diagnosing the state of a heart, including the case of treatment by nerve stimulation, and of aiding appropriate heart treatment by nerve stimulation.

An additional object of the present invention is to provide a heart treatment device that can enhance the therapeutic effect of the nerve stimulation on the heart by clearly ascertaining the therapeutic effect thereof.

In order to achieve the above-described objects, the present invention employs the following solutions.

A first aspect of the present invention is a cardiac-event processor that includes a storing unit that stores a time history of cardiac events, including heartbeats, in association with the presence/absence of nerve stimulation; a heart rate calculator that calculates a heart rate for when each heartbeat is detected, on the basis of the time history of the cardiac events stored in the storing unit; and a frequency data generator that separately adds up frequencies of the heart rates calculated by the heart rate calculator for the cases with and without the nerve stimulation.

A second aspect of the present invention is a heart treatment device that includes heartbeat detector for detecting heartbeats with electrodes disposed on a heart; nerve stimulator for stimulating a nerve which suppresses pulsing of the heart, on the basis of the heartbeats detected by the heartbeat detector; and a storing unit that stores a time history of cardiac events, including the heartbeats detected by the heartbeat detector, in association with the presence/absence of the nerve stimulation by the nerve stimulator.

BRIEF DESCRIPTION OF THE SEVERAL VIEWS OF THE DRAWINGS

FIGS. 7A and 7B are example histograms generated by the cardiac-event processor in FIG. 1, wherein FIG. 7A is a histogram for the case in which nerve stimulation is not being performed, and FIG. 7B is a histogram for the case in which nerve stimulation is being performed.

FIGS. 12A and 12B are another modification of the histogram generated by the cardiac-event processor of the first or second embodiment, wherein FIG. 12A is a histogram for the case in which nerve stimulation is not being performed, and FIG. 12B is a histogram for the case in which nerve stimulation is being performed.

FIGS. 14A and 14B are example histograms generated by the cardiac-event processor of the first or second embodiment when the vagus nerve is stimulated by the heart treatment device of the first or second embodiment with differing stimulation intensities, wherein FIG. 14A shows a case with an appropriate stimulation intensity, and FIG. 14B shows a case with excessive stimulation intensity.

DETAILED DESCRIPTION OF THE INVENTION

A cardiac-event processor 1 and a heart treatment device 2 according to a first embodiment of the present invention will be described below, with reference to FIGS. 1 to 7B.

Figure 1:
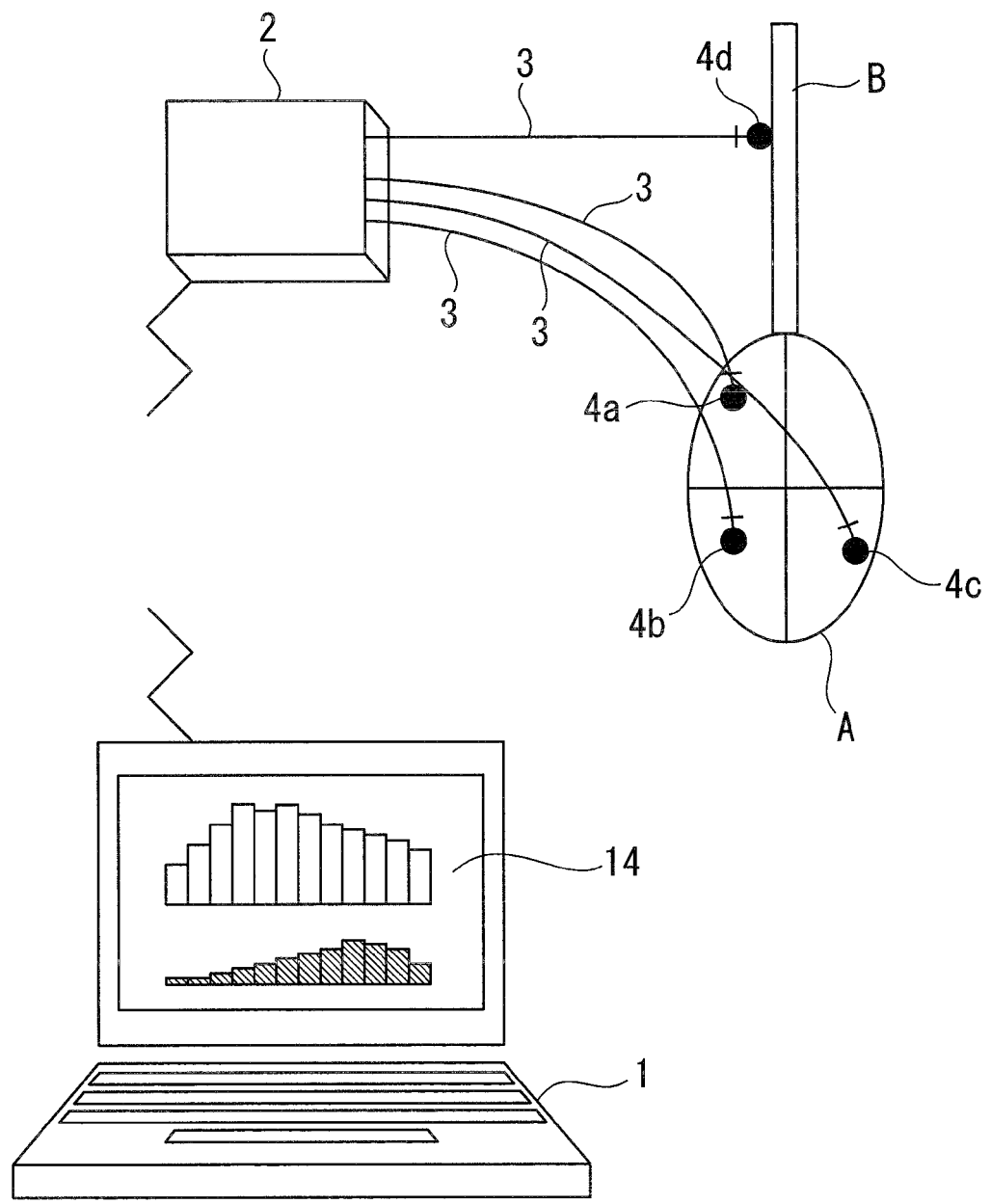
FIG. 1 is an overall configuration diagram of a cardiac-event processor and an implantable heart treatment device according to a first embodiment of the present invention.

As shown in FIG. 1, the cardiac-event processor 1 according to this embodiment processes cardiac-event information received wirelessly from a heart treatment device 2. In this embodiment, the cardiac-event processor 1 is assumed to be a portable computer disposed near the patient. The heart treatment device 2 is assumed to be an implantable medical device (IMD) 2 which is implanted inside the body of a patient.

Figure 2:
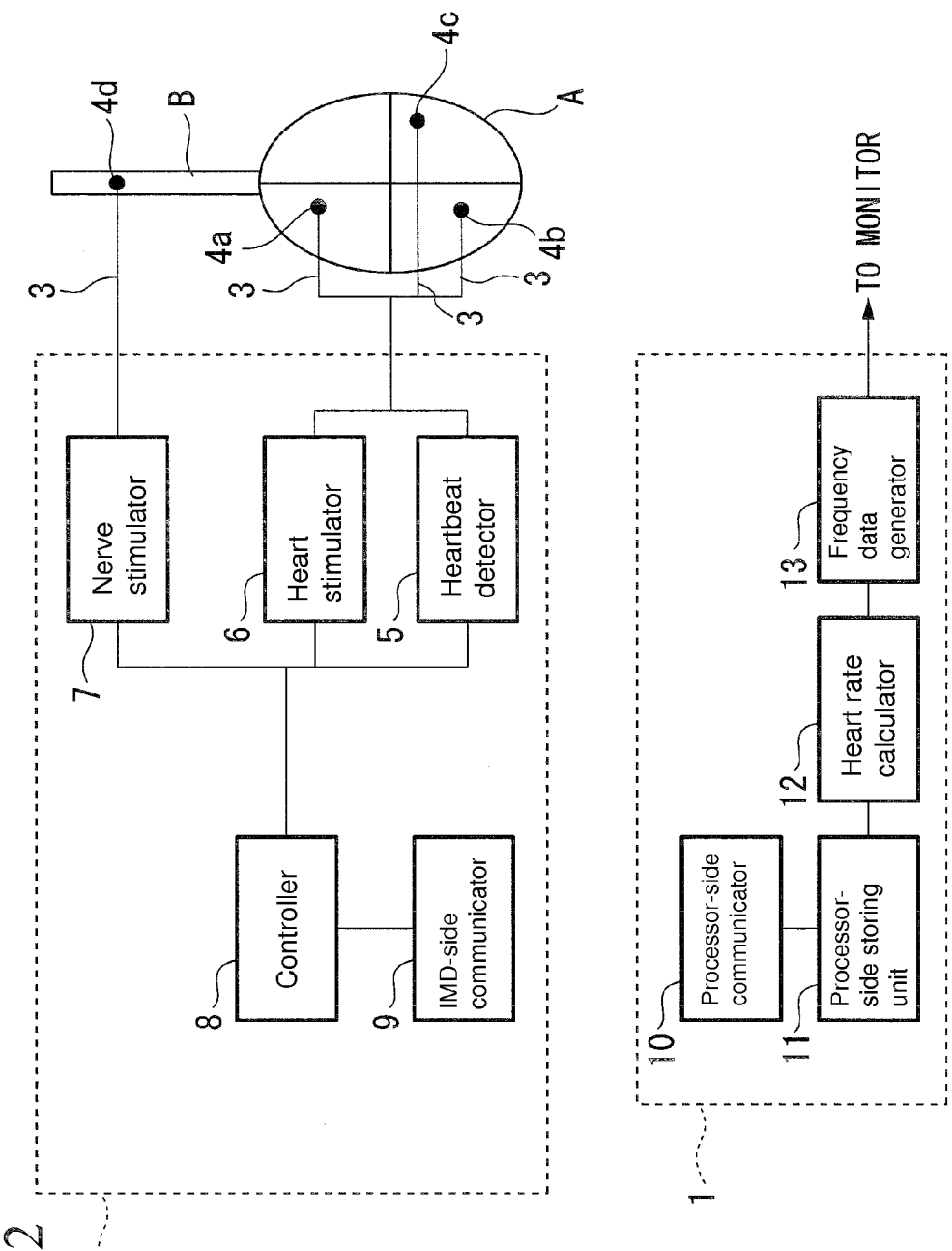
FIG. 2 is a block diagram showing functions of the cardiac-event processor and the heart treatment device in FIG. 1.

FIG. 2 is a block diagram showing functions of the cardiac-event processor 1 and the IMD 2.

As shown in FIG. 2, the IMD 2 is provided with a heartbeat detector 5 and a heart stimulator 6 that are connected to a heart A via leads 3, a nerve stimulator 7 that is connected to a vagus nerve B via another lead 3, a controller 8 that controls the operation of the heart stimulator 6 and the nerve stimulator 7, and an IMD-side communicator 9 that wirelessly communicates with the cardiac-event processor 1.

The leads 3 are each provided with electrodes 4a to 4d at their tips. The electrodes 4a to 4d are individually disposed at the right atrium, the right ventricle, the left ventricle, or the vagus nerve B that is found near the heart A.

The heartbeat detector 5 detects changes in electric potential of the electrodes 4a to 4c disposed at the right atrium, the right ventricle, and the left ventricle. Then, when the magnitude or rate of change of the detected electric potential exceeds a predetermined threshold, the heartbeat detector 5 determines that an R wave has appeared, thereby detecting a heartbeat.

The heart stimulator 6 generates a pacing pulse that stimulates the heart A to cause contraction and supplies the heart A with the generated pacing pulse via the individual electrodes 4a to 4c. Accordingly, the pulsing of the heart A is paced, thereby treating bradycardia.

The nerve stimulator 7 generates stimulation pulses that stimulate the vagus nerve B and supplies the vagus nerve B with the stimulation pulses via the electrode 4d. Accordingly, pulsing of the heart A is suppressed by the excitation of the vagus nerve B, thereby treating tachycardia and fibrillation. At this time, the nerve stimulator 7 supplies the stimulation pulses of a predetermined pulse width X at time intervals with a predetermined period Y over a predetermined duration time Z.

The controller 8 has a timer. The controller 8 measures the time interval between one heartbeat and the next heartbeat while resetting the timer count to zero every time the heartbeat detector 5 detects a heartbeat. When the measured timer count is at or above a threshold, i.e., when the heart rate is at or below a predetermined value, the controller 8 instructs the heart stimulator 6 to supply the heart A with the pacing pulse.

In addition, when the next heartbeat is detected before the measured timer count reaches the threshold, i.e., when the heart rate exceeds a predetermined value, the controller 8 instructs the nerve stimulator 7 to begin supplying the vagus nerve B with the stimulation pulses, thereby beginning the nerve stimulation. At this time, the controller 8 calculates an average count value of the timer count measured from the beginning of stimulation-pulse supply until a predetermined waiting time W has passed after the end of the stimulation-pulse supply.

Figure 3:
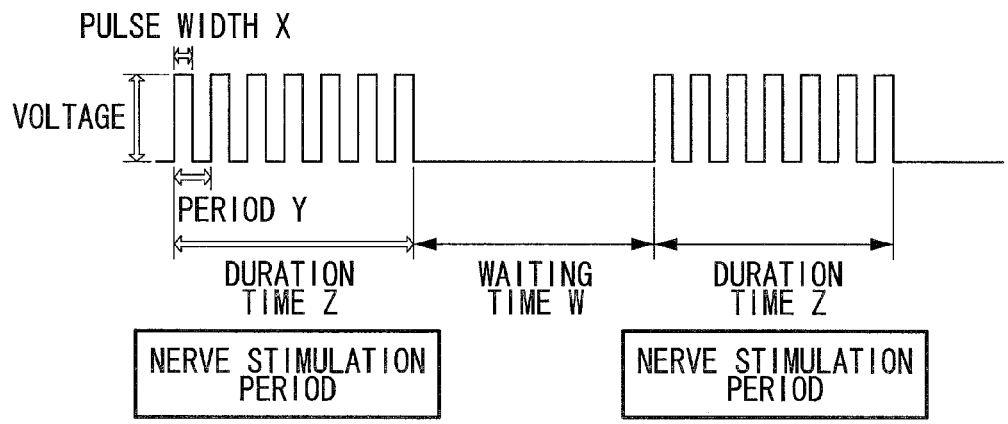
FIG. 3 is a diagram explaining a nerve stimulation method of the heart treatment device in FIG. 1.

For example, as shown in FIG. 3, the controller 8 supplies the stimulation pulses over the duration time Z (10 seconds in this case), waits for the waiting time W (50 seconds in this case) after the end of the stimulation-pulse supply, and calculates an average value of the timer count measured during the 60-second period since the beginning of the stimulation-pulse supply. The calculated average value indicates whether the heart rate has been lowered to a stable state due to the nerve stimulation or whether the heart rate remains raised.

When the calculated average value of the count is at or above a threshold, the controller 8 terminates the nerve stimulation. On the other hand, when the calculated average value of the count is below the threshold, the controller 8 gives the instruction to supply the vagus nerve B with the stimulation pulses for 10 seconds again, and repeats the nerve stimulation at 50-second intervals until the average value of the count reaches or exceeds the threshold.

In addition, the controller 8 sequentially sends the counts obtained immediately before resetting the timer to the IMD-side communicator 9. The IMD-side communicator 9 transmits the count information to the cardiac-event processor 1 in the order in which it is sent from the controller 8. At this time, for the count measured while the duration time Z additionally passes from the time at which a predetermined delay time Td has passed from the beginning of the stimulation-pulse supply, the controller 8 adds a with-nerve-stimulation tag and outputs it to the IMD-side communicator 9.

Figure 4:
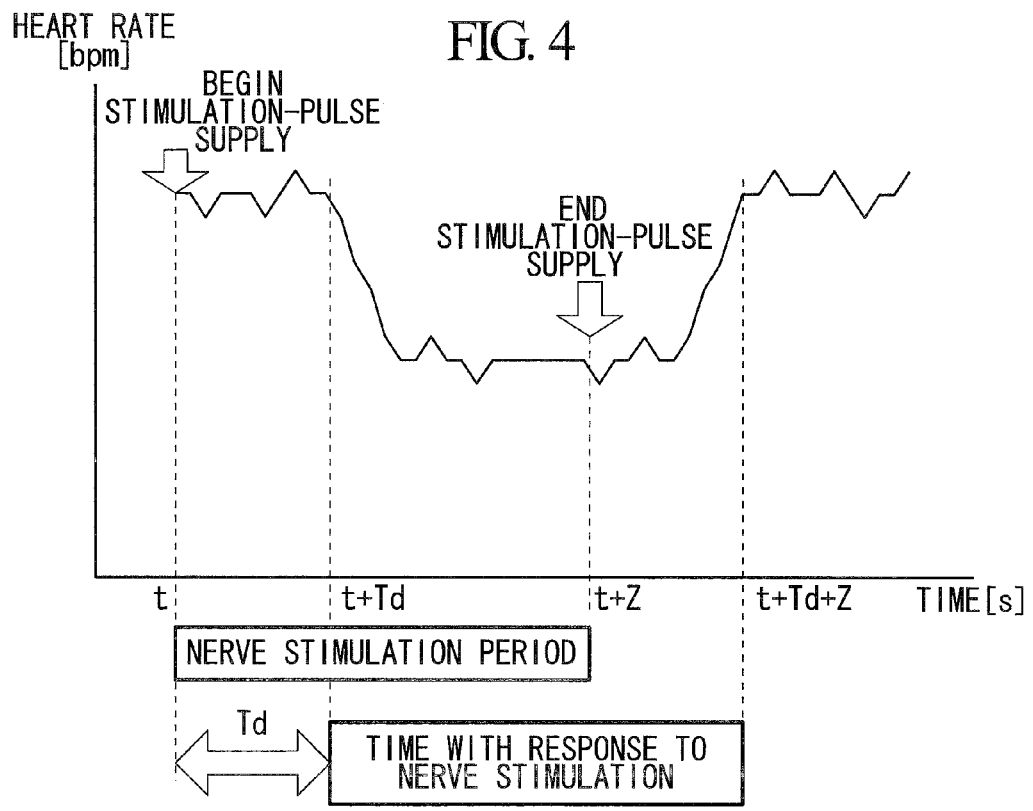
FIG. 4 is a diagram explaining the relationship between nerve stimulation by the heart treatment device in FIG. 1 and changes in heart rate brought about by the nerve stimulation.

When the nerve stimulator 7 begins to output the stimulation pulses, the heart A shows a delayed response to the stimulation pulses with the delay time Td, as shown in FIG. 4. This is because it takes conveyance time required for the stimulation pulses to reach the vagus nerve B and biological response time required for the suppression of pulsing to occur through the vagus nerve excitation. That is, the with-nerve-stimulation tag is added to the count when the heart A is actually responding to the stimulation pulses.

The cardiac-event processor 1 according to this embodiment is provided with a processor-side communicator 10 that wirelessly communicates with the IMD 2, a processor-side storing unit 11 that stores time history of the cardiac-event information acquired from the IMD 2, a heart rate calculator 12 that calculates the heart rates from the time history of the cardiac events stored in the processor-side storing unit 11, and a frequency data generator 13 that generates a histogram showing a frequency distribution of the heart rates from the heart rates calculated by the heart rate calculator 12.

The processor-side communicator 10 inputs the timer-count information sequentially transmitted from the IMD 2 to the processor-side storing unit 11 in order of reception.

The processor-side storing unit 11 stores the timer count information in order of input from the processor-side communicator 10 and accumulates the time history of the heartbeat. At this time, when the timer count information has the with-nerve-stimulation tag, the processor-side storing unit 11 stores the tag information together with the timer count information.

The heart rate calculator 12 calculates the heart rates by dividing each of the timer counts stored in the processor-side storing unit 11 by 60 seconds.

The frequency data generator 13 divides the heart rates into a plurality of bins and adds up the frequencies of the bins to which the heart rates calculated by the heart rate calculator 12 belong. At this time, the frequency data generator 13 separately adds up the frequencies for the heart rates calculated from the timer counts with the with-nerve-stimulation tag and the heart rates calculated from the timer counts without the tag. Accordingly, frequency data indicating frequency distributions of the heart rates are separately generated for the heart rates when the heart A is supplied with the stimulation pulses and is responding to the stimulation pulses, and for the heart rates at other times. The frequency data generator 13 generates separate histograms from the respective sets of the generated frequency data.

Figure 5:
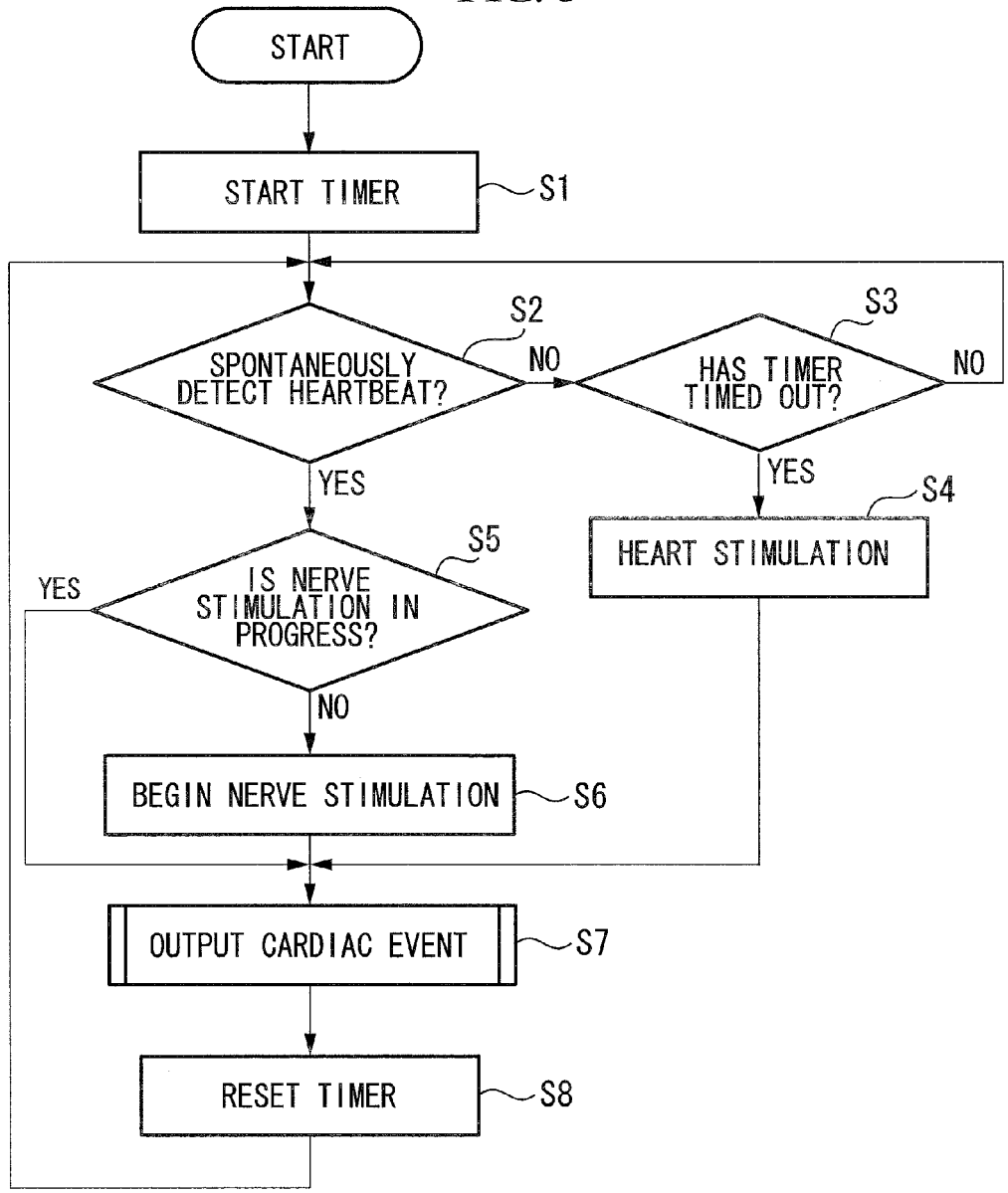
FIG. 5 is a flowchart explaining the operation of the heart treatment device in FIG. 1.
Figure 6:
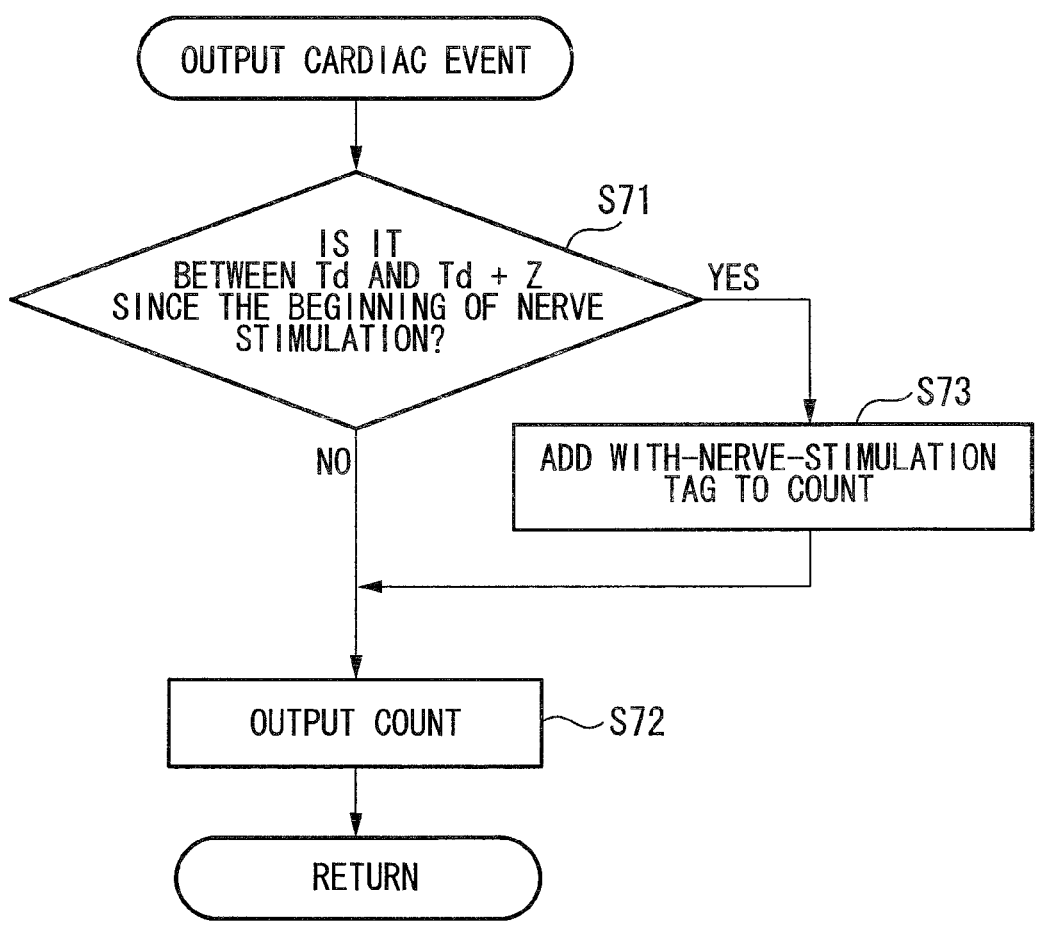
FIG. 6 is a flowchart showing a cardiac-event output routine of the flow chart in FIG. 5.

The operation and effects of the thus-configured cardiac-event processor 1 and the IMD 2 will be described below, with reference to the flow charts of FIGS. 5 and 6.

The IMD 2 according to this embodiment begins measuring time with the timer (Step S1) and determines whether or not a heartbeat is detected (Step S2). Here, when the heartbeat is not detected within a predetermined period of time (Step S3), the IMD 2 stimulates the heart A to pace the pulsing of the heart A (Step S4). On the other hand, when the heartbeat is detected within the predetermined period of time, if the nerve stimulation is in progress (Step S5), i.e., the nerve stimulation has been already begun but a predetermined waiting time W has not yet passed, the IMD 2 does not perform the nerve stimulation; and, if the nerve stimulation is not in progress (Step S5), the IMD 2 begins the nerve stimulation (Step S6).

Subsequently, the IMD 2 outputs the cardiac-event information to the cardiac-event processor 1 (Step S7). That is, the IMD 2 determines whether or not the time at which the heartbeat is detected falls within a period during which the heart A is responding to the stimulation pulses (Step S71), and directly outputs the timer count to the cardiac-event processor 1 if it does not fall within a period during which the heart A is responding (Step S72). On the other hand, if the time at which the heartbeat is detected falls within the period during which the heart A is responding to the stimulation pulses, the IMD 2 outputs the timer count to the cardiac-event processor 1 (Step S72) having the with-nerve-stimulation tag added thereto (Step S73).

Then, the IMD 2 resets the timer count to zero (Step S8).

In the manner described above, the history of the timer count is accumulated in the cardiac-event processor 1. The cardiac-event processor 1 calculates the heart rates from the timer count and adds up the frequencies of the bins to which the calculated heart rates correspond, while sorting them according to the presence/absence of the with-nerve-stimulation tag.

The cardiac-event information accumulated in the cardiac-event processor 1 for a certain period of time is displayed as a histogram by being output from the cardiac-event processor 1 to a monitor 14, for example, at the time of a periodical medical check by a doctor. Viewing the histogram displayed on the monitor 14, the doctor diagnoses the state of the heart A of the patient; considers whether or not the settings of the IMD 2 are appropriate; and adjusts the intensity, etc. of the stimulation pulses of the IMD 2 if needed.

Figure 7A:
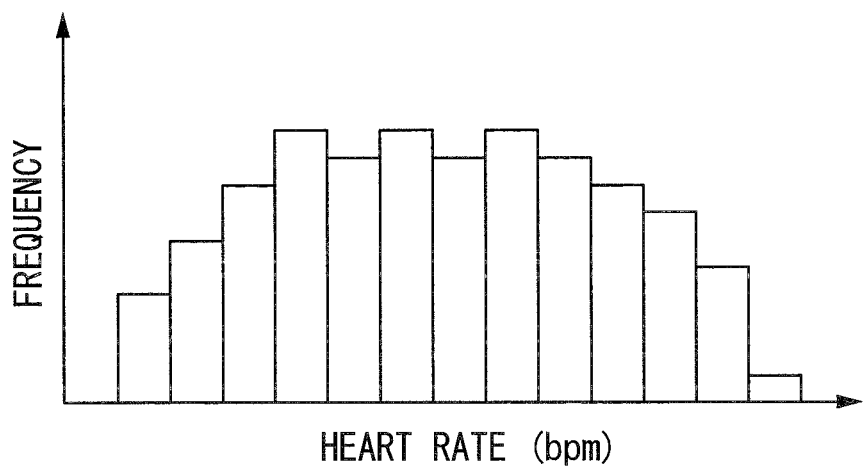
Figure 7B:
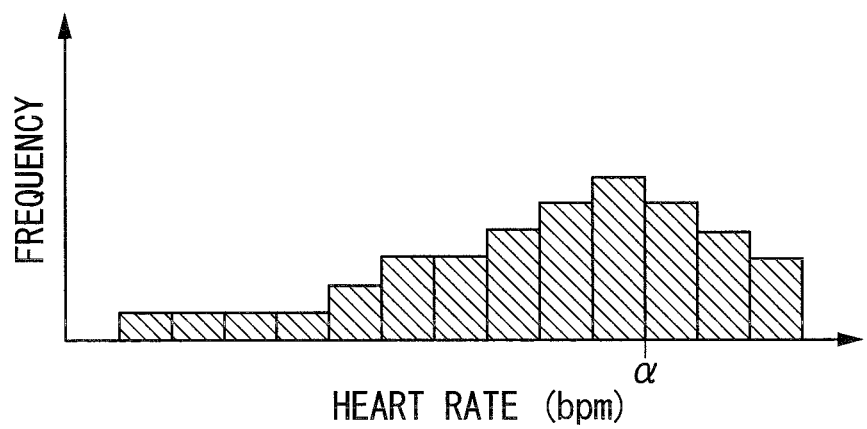

FIGS. 7A and 7B show example histograms to be displayed on the monitor 14. FIG. 7A shows a histogram for the heart rates without the nerve stimulation. That is, FIG. 7A shows the state of the heart A when the heart A is not responding to the stimulation pulses, and the distribution of the heart rates indicates the presence/absence of various types of arrhythmia and its occurrence frequency. FIG. 7B shows a histogram for when the heart A is responding to the stimulation pulses. For example, in the case in which the IMD 2 is set to output the stimulation pulses when the heart rates exceed a threshold $\alpha$, a distribution of frequencies of heart rates skewed toward a region lower than the threshold a indicates that the pulsing is effectively suppressed by the stimulation pulses and that the settings of the stimulation pulses are appropriate.

In this way, according to this embodiment, an advantage is afforded in that a doctor, with a glance at the histogram, can clearly recognize and can correctly diagnose a state of the heart A, such as the presence/absence of the occurrence of arrhythmia, etc. An additional advantage is afforded in that the histogram allows the doctor to accurately determine the presence/absence of a therapeutic effect of the nerve stimulation and whether or not its settings are appropriate. A further advantage is afforded in that, because the settings of the IMD 2, such as the intensity of the stimulation pulses, can be appropriately adjusted, treatment of the heart A can be aptly aided.

Figure 8:
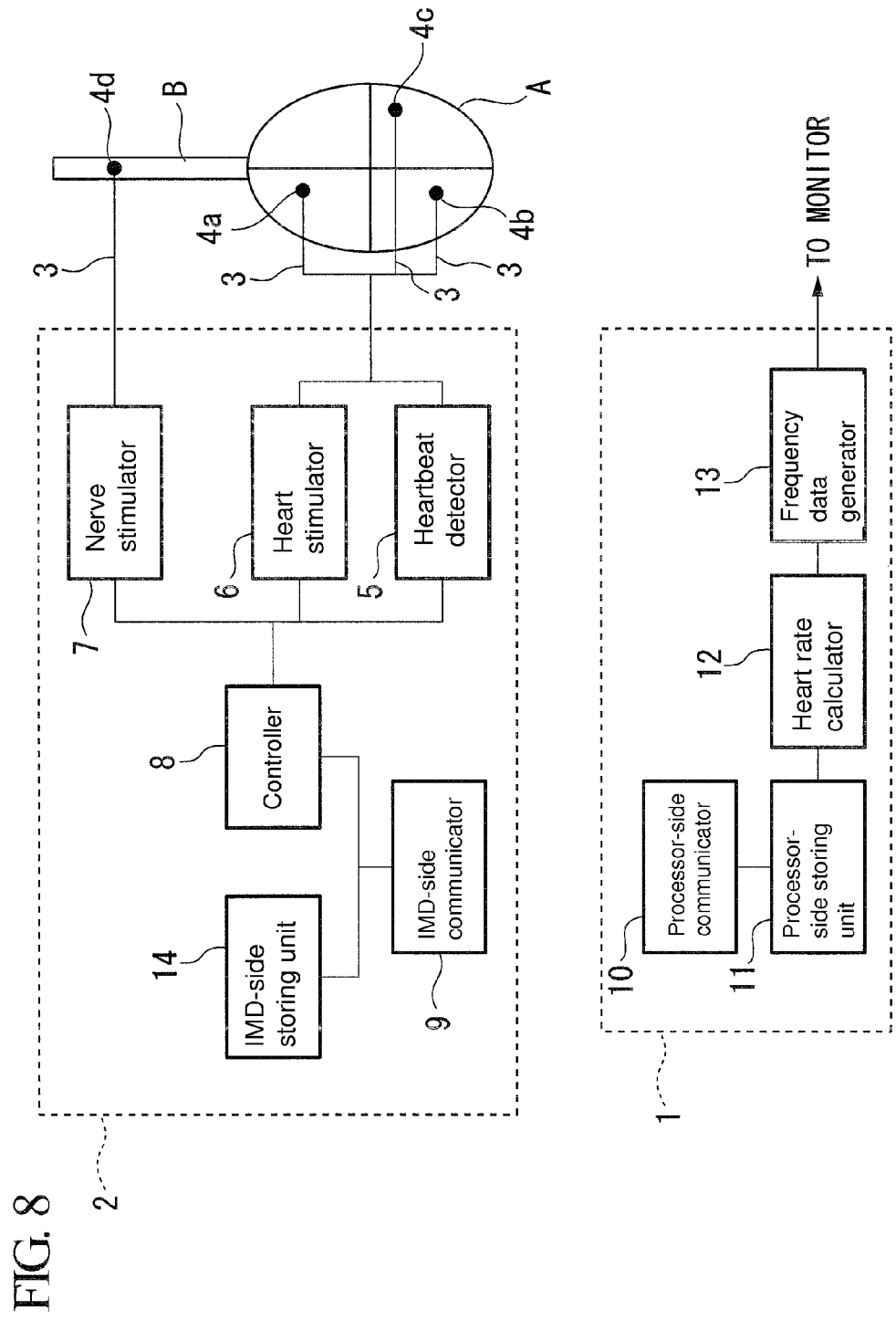
FIG. 8 is a block diagram showing functions of a cardiac-event processor and a heart treatment device according to a second embodiment of the present invention.
Figure 9:
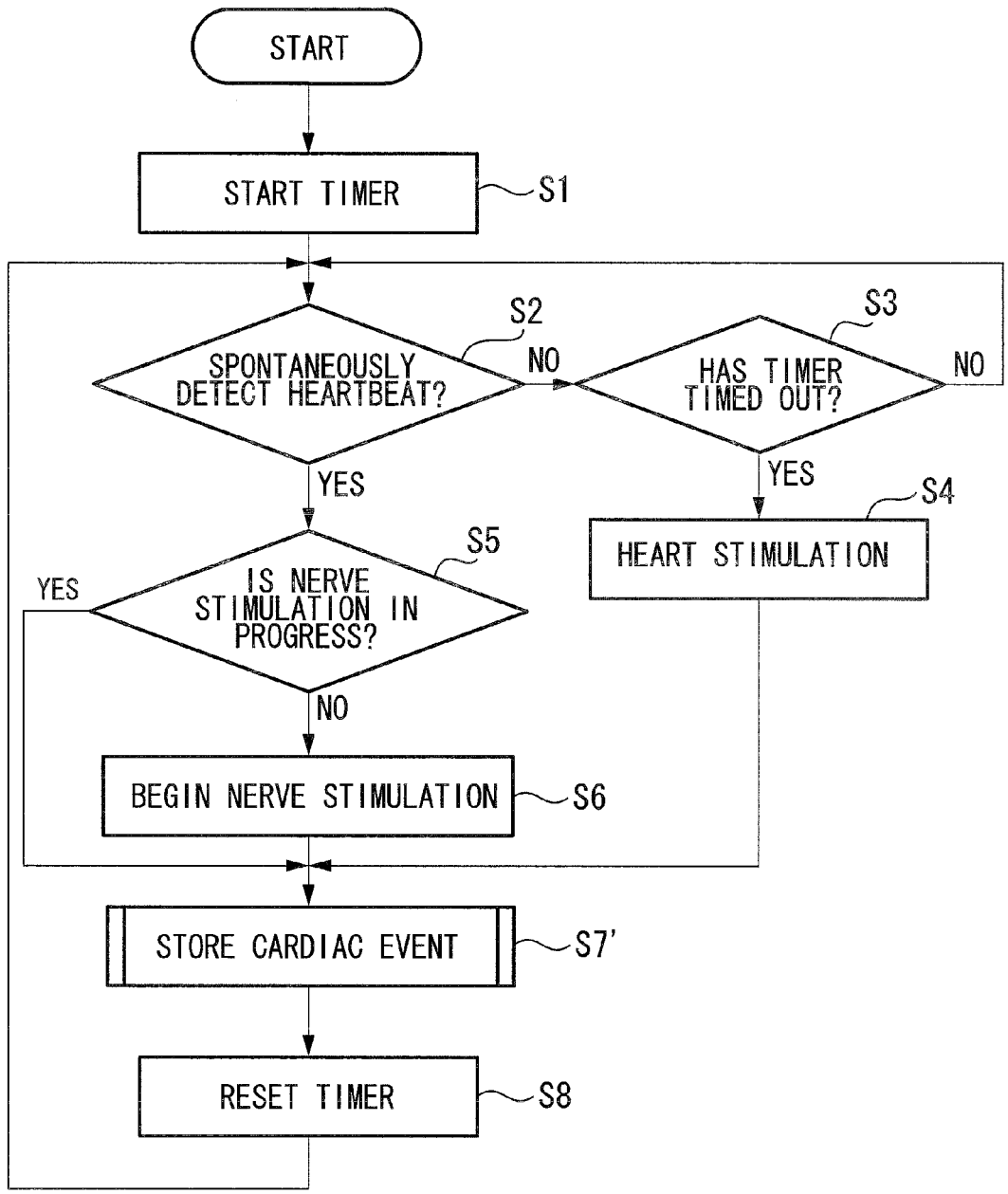
FIG. 9 is a flowchart explaining the operation of the heart treatment device in FIG. 8.
Figure 10:
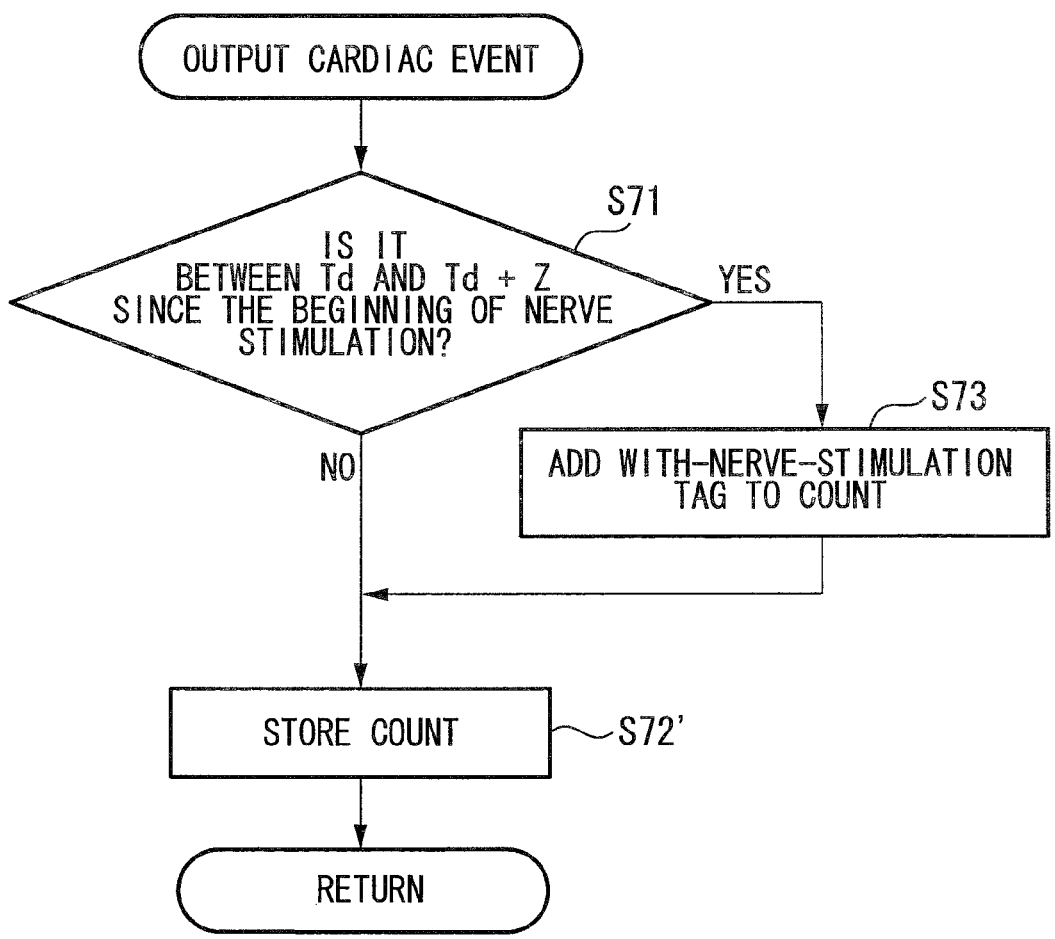
FIG. 10 is a flowchart showing a cardiac-events storing routine of the flowchart in FIG. 9.

Next, a cardiac-event processor 1 and a heart treatment device (IMD) 2 according to a second embodiment of the present invention will be described below, with reference to FIGS. 8 to 10.

In this embodiment, points that differ from the first embodiment will be mainly described, and components common with the first embodiment will be given the same references, and a description thereof will be omitted.

As shown in FIG. 2, the cardiac-event processor 1 and the IMD 2 according to this embodiment differ from the first embodiment in that the IMD 2 is provided with an IMD-side storing unit 14 that stores cardiac events, and the IMD 2 accumulates cardiac-event information. The cardiac-event information accumulated by the IMD 2 for a certain period of time is output to the cardiac-event processor 1, which is disposed outside the body of the patient, where it is statistically processed.

A controller 8 sequentially inputs the counts obtained immediately before resetting the timer to the IMD-side storing unit 14. The IMD-side storing unit 14 accumulates time history information of the heartbeat by storing the count information in order in which it is input from the controller 8. At this time, for the count measured while duration time Z additionally passes from the time at which a predetermined delay time Td has passed from the beginning of the stimulation-pulse supply, the controller 8 adds a with-nerve-stimulation tag and inputs it to the IMD-side storing unit 14.

The operation and effect of the thus-configured cardiac-event processor 1 and the IMD 2 will be described below, with reference to flowcharts in FIGS. 9 and 10.

From Step S1 to Step S6, the IMD 2 according to this embodiment operates similarly to that in the first embodiment.

The IMD 2 stores the cardiac-event information (Step S7'), following heart stimulation (Step S4) or nerve stimulation (Step S6). That is, similarly to the procedure performed by the cardiac-event processor in the first embodiment, the IMD 2 directly stores the timer count except for the period during which the heart is responding to the stimulation pulses (Step S72). On the other hand, for the period during which the heart is responding to the stimulation pulses, the IMD 2 stores (Step S72') the timer count having the with-nerve-stimulation tag added thereto (Step S73). Then, the IMD 2 resets the timer count to zero (Step S8).

In the manner described above, the history of the timer count is accumulated in the IMD 2.

The cardiac-event information accumulated in the IMD 2 for a certain period of time is output to the cardiac-event processor 1 installed, for example, at a hospital. The cardiac-event processor 1 stores the cardiac-event information acquired from the IMD 2 in a processor-side storing unit 11 and, similarly to the first embodiment, generates separate histograms of the heart rates depending on the presence/absence of the nerve stimulation.

In this way, according to this embodiment, similarly to the first embodiment, advantage are afforded in that, with a glance at the histogram, a doctor can clearly recognize and can correctly diagnose the state of the heart A, and also it is possible to accurately determine the presence/absence of a therapeutic effect of the nerve stimulation and whether or not its settings are appropriate. Accordingly, an additional advantage is afforded in that the therapeutic effect on the heart A can be enhanced by appropriately adjusting the settings of the IMD 2. Furthermore, according to this embodiment, by accumulating the cardiac-event information in the IMD 2, a patient does not need to constantly carry the cardiac-event processor 1; therefore, an advantage is afforded in that the burden on the patient can be reduced.

Figure 11:
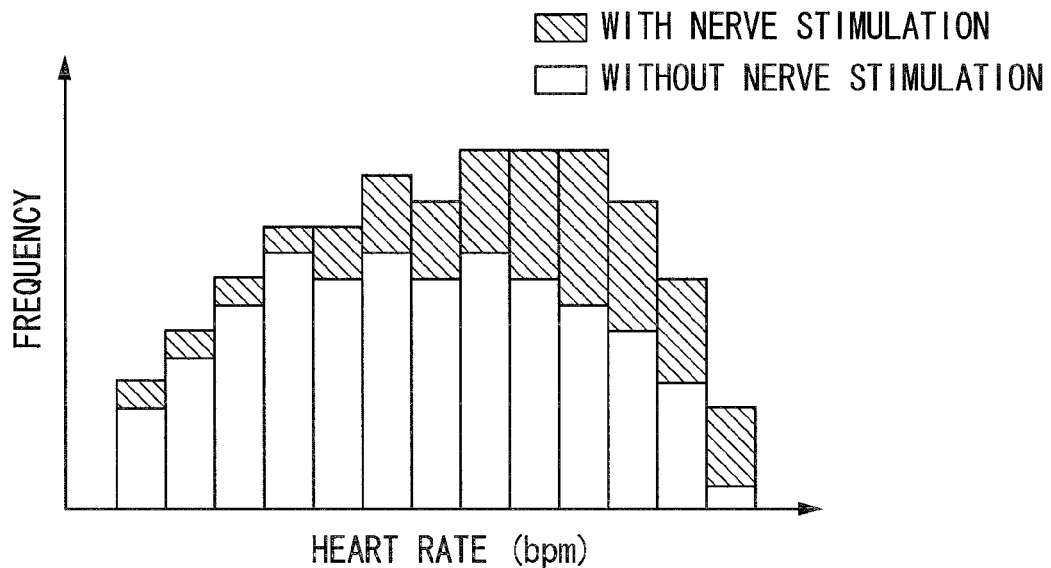
FIG. 11 is a modification of the histogram generated by the cardiac-event processor of the first or second embodiment.

In the above-described first and second embodiments, the frequency distribution of the heart rates with the nerve stimulation and the frequency distribution of the heart rates without the nerve stimulation may be displayed as a single histogram, as shown in FIG. 11. In this case, frequencies with the nerve stimulation and the frequencies without it are visually distinguished even in the single histogram by displaying them using differing appearances such as hatching, colors, etc. By doing so, an accurate diagnosis of the state of the heart A is also possible, and, additionally, it is possible to clearly know the effects of the nerve stimulation. Furthermore, for each bin of the histogram, a frequency ratio between with and without the nerve stimulation can be recognized at a glance.

Figure 12A:
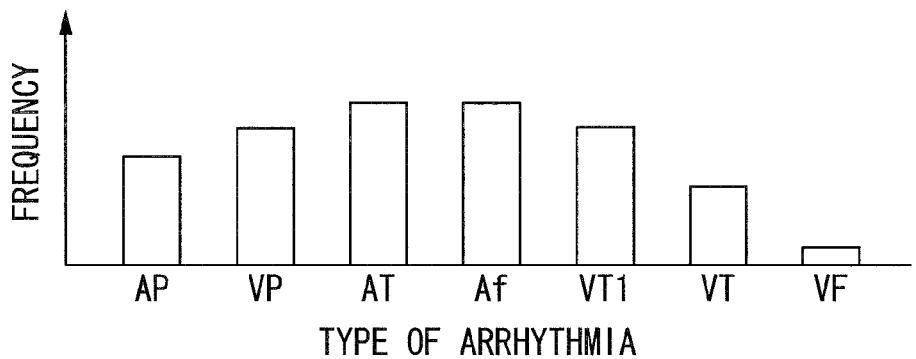
Figure 12B:
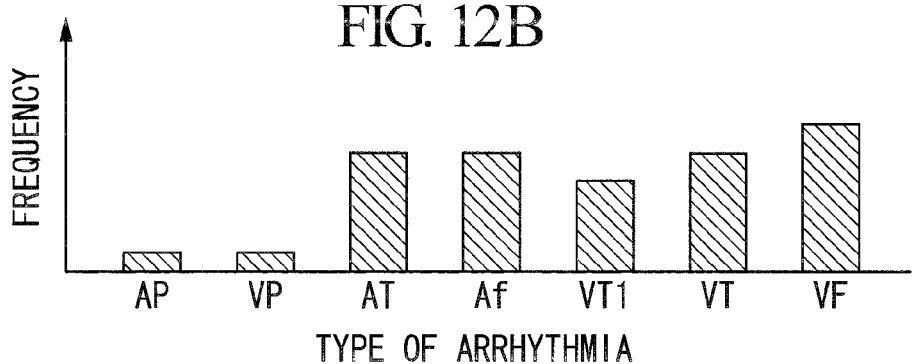

In the above-described first and second embodiments, as shown in FIGS. 12A and 12B, a histogram may be generated for showing frequencies of arrhythmia by its types, instead of the frequency distribution of the heart rates. FIG. 12A shows a histogram for when the nerve stimulation is not supplied and FIG. 12B shows a histogram for when the nerve stimulation is supplied.

In this case, the cardiac-event processor 1 stores thresholds set for each type of arrhythmia in the frequency data generator 13. The frequency data generator 13 determines to which type of arrhythmia the heart rates calculated by the heart rate calculator 12 belong, on the basis of the stored thresholds, and adds up the frequencies of the determined type of arrhythmia. By doing so, the state of the heart A and the effect of the nerve stimulation can also be clearly ascertained from each histogram. Note that, in FIGS. 12A and 12B, AP is atrial bradycardia, VP is ventricular bradycardia, AT is atrial tachycardia, Af is atrial fibrillation, VT1 is ventricular tachycardia with relatively slow heart rate, VT is ventricular tachycardia with relatively fast heart rate, and VF is ventricular fibrillation.

Figure 13:
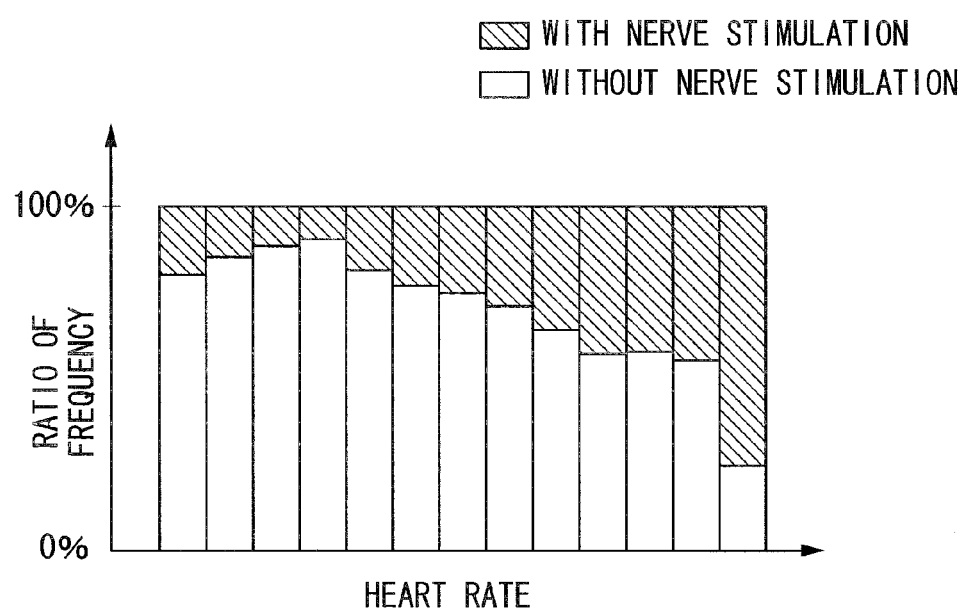
FIG. 13 is a modification of a processing result of the cardiac-event processor of the first or second embodiment.

In the above-described first and second embodiments, instead of the histogram showing the frequency distribution of the heart rates, a ratio distribution may be generated, as shown in FIG. 13, which shows frequency ratios between with nerve stimulation and without nerve stimulation, by normalizing all frequencies in each bin to the same value. In this case, the frequency data generator 13 calculates ratios between with and without the nerve stimulation for each bin by separately dividing the frequencies of with and without the nerve stimulation by the total frequency of the bin in question. Then, the frequency data generator 13 generates a ratio distribution from the calculated ratios and displays it. By doing so, the frequency ratios of heartbeats with and without the nerve stimulation can be easily compared between the bins.

In the above-described first and second embodiments, the controller 8 may control the magnitude of the stimulation-pulse energy according to the heart rates. By doing so, in the case of tachycardia or fibrillation, the therapeutic effect can be enhanced by stimulating the vagus nerve B more strongly as the heart rate increases. In this case, the cardiac-event processor 1 or the IMD 2 may reflect the magnitude of the stimulation-pulse energy in histograms.

For example, the controller 8 performs the nerve stimulation at three intensity levels of weak, medium, and strong, by decreasing or increasing the pulse width of the stimulation pulses generated by the nerve stimulator 7. Here, the controller 8 stimulates the vagus nerve B with weak stimulation when the heart rate is at or above the threshold $\alpha$ and less than a threshold $\beta$, with medium stimulation when the heart rate is at or above the threshold $\beta$ and less than a threshold $\gamma$, and with strong stimulation when the heart rate is at or above the threshold $\gamma$. The controller 8 outputs the nerve stimulation intensity information to the IMD-side communicator 9 along with the with-stimulation tag in association with the timer count, or stores it in the IMD-side storing unit 14. The frequency data generator 13 adds up the frequencies of the heart rates, sorting them by the nerve stimulation intensity information added to the count, and displays a histogram in which different display appearances such as hatching, colors, etc. are used in accordance with the nerve stimulation intensity.

FIGS. 14A and 14B show example histograms generated in this way for when the nerve stimulation is applied. FIG. 14A shows a case in which the nerve stimulation intensity is appropriately adjusted, and FIG. 14B shows a case in which the nerve stimulation intensity is inappropriate. In FIG. 14A, the frequencies of intensities are distributed in regions lower than the respective thresholds $\alpha$, $\beta$, and $\gamma$ for the heart rates. This indicates that the heart rates are lowered by all levels of the nerve stimulation intensity.

In FIG. 14B, on the other hand, for the medium nerve stimulation intensity, the frequency is distributed only in a region where the heart rates are higher than the threshold $\beta$. This indicates that the stimulation intensity is insufficient to manifest the effect of lowering the heartbeat. On the other hand, for the strong nerve stimulation intensity, the frequency is distributed so as to reach a region where the heart rates are considerably lower than the threshold $\gamma$. This indicates that the pulsing is excessively suppressed because the stimulation intensity was too strong, thereby causing the heart rates to be excessively lowered.

By doing so, the effects of the nerve stimulation by the IMD 2 and its extent can be clearly recognized for each intensity at a glance, and it is possible to provide an aid so that even complicated stimulation intensity setting can be appropriately performed.

In the above-described first and second embodiments, the IMD 2 may output the heartbeat to the cardiac-event processor 1 or may store it in the IMD-side storing unit 14, in association with the presence/absence of the heart stimulation.

In this case, the frequency data generator 13 adds up the heart rates calculated by the heart rate calculator 12, sorting them into with-nerve stimulation, with-heart-stimulation, and without-nerve stimulation/heart-stimulation. By doing so, the state of the heart A of a patient can be more accurately diagnosed by ascertaining the occurrence frequency of bradycardia from the frequency of the heart rate with the heart stimulation.

In the above-described embodiments, the IMD 2 may be provided with a delay-time calculator that calculates the delay time Td. In this case, the controller (delay-time calculator) 8 may also serve dual purpose as the delay-time calculator.

For example, functional expressions are set in the controller 8 for calculating the delay time Td from the transmission speed of excitation of the vagus nerve B, the length of the vagus nerve B from the electrode 4d to the heart A, and the biological response time of the heart A to the excitation transmitted from the vagus nerve B.

Then, when the IMD 2 is installed inside the body of a patient, the length of the vagus nerve B from the installation position of the electrode 4d to the heart A is estimated, and this value is input to the controller 8 to calculate the delay time Td appropriate for that patient. By doing so, the heartbeat with the stimulation is more accurately associated with the time at which the heart A responds to the nerve stimulation, thereby making it possible to more accurately assess the therapeutic effect of the nerve stimulation.

Note that, the following aspects are derived from the above-described first and second embodiments.

A first aspect of the embodiments of the present invention provides a cardiac-event processor that includes a storing unit that stores a time history of cardiac events, including heartbeats, in association with the presence/absence of nerve stimulation; a heart rate calculator that calculates a heart rate for when each heartbeat is detected, on the basis of the time history of the cardiac events stored in the storing unit; and a frequency data generator that separately adds up frequencies of the heart rates calculated by the heart rate calculator for the cases with and without the nerve stimulation.

According to this aspect, upon input of the time-history information of the cardiac events to the cardiac-event processor, the information is stored in the storing unit; of the stored cardiac events, the time history of the heartbeat is used by the heart rate calculator to calculate the heart rates; and the frequency data that represents a frequency distribution of the heart rates is generated by the frequency data generator by adding up the frequencies of the calculated heart rates. Therefore, the state of a heart such as the presence/absence of arrhythmia can be diagnosed by outputting the generated frequency data from the cardiac-event processor.

In this case, the frequency of the heart rates with the nerve stimulation and the frequency of the heart rates without the nerve stimulation are separately added up. Therefore, it is possible to correctly diagnose a state of a heart of a patient from the frequency data of the heart rates without the nerve stimulation. In addition, the frequency data of the heart rates with the nerve stimulation makes it possible to clearly ascertain the presence/absence of a therapeutic effect of the nerve stimulation and its extent, thereby making it possible to aid heart treatment with the nerve stimulation.

In the above-described first aspect, the frequency data generator may generate a histogram that shows the frequency distribution of the heart rates.

By doing so, the processing results obtained by the cardiac-event processor are output as a histogram, making it possible to ascertain, at a glance, the state of the heart and the therapeutic effect of the nerve stimulation.

In the above-described first aspect, the configuration may include a display unit that separately displays the frequencies of the heart rates with the nerve stimulation and the frequencies of the heart rates without the nerve stimulation, which are added up by the frequency data generator.

By doing so, it is possible to more easily ascertain the state of the heart without the nerve stimulation and the therapeutic effect of the nerve stimulation.

In this configuration, the frequency data generator may add the frequencies of the heart rates with the nerve stimulation to the frequencies of the heart rates without the nerve stimulation to generate a histogram showing a frequency distribution of the overall heart rates, and the display unit may display the histogram generated by the frequency data generator in such a way that the frequencies of the heart rates are displayed with different display appearances for the cases with and without the nerve stimulation.

By doing so, the balance between the heartbeats due to the nerve stimulation and the rest of the heartbeats can be ascertained at a glance.

In the above-described first aspect, the frequency data generator may add the frequencies of the heart rates with the nerve stimulation to the frequencies of the heart rates without the nerve stimulation, and may normalize the frequencies of the heart rates with the nerve stimulation and the frequencies of the heart rates without the nerve stimulation by dividing them by the sum of the frequencies.

By doing so, it is possible to easily compare ratios of the frequencies of the heart rates with and without the nerve stimulation among different heart rates.

In the above-described first aspect, in the case where the nerve stimulation is supplied, the storing unit may store the time history of the heartbeats in association with the intensity of the nerve stimulation, and the frequency data generator may add up the frequencies of the heart rates with the nerve stimulation by sorting them according to the magnitude of the intensities of the nerve stimulation.

By doing so, even when the nerve stimulation is performed while changing its intensity according to the state of the heart, it is possible to aid an appropriate adjustment for individual intensities of the nerve stimulation by ascertaining the therapeutic effect of the nerve stimulation of the respective intensities.

In the above-described aspect, the storing unit may store the nerve stimulation in association with the heartbeat detected a predetermined time after the nerve stimulation.

By doing so, the nerve stimulation is associated with the heartbeat when the heart is actually responding to the nerve stimulation, thereby making it possible to more accurately ascertain the therapeutic effect of the nerve stimulation.

A second aspect of the embodiments of the present invention is a heart treatment device that includes a heartbeat detector that detects heartbeats with electrodes disposed on a heart; a nerve stimulator that stimulates a nerve which suppresses the pulsing of the heart, on the basis of the heartbeats detected by the heartbeat detector; and a storing unit that stores a time history of cardiac events, including the heartbeats detected by the heartbeat detector, in association with the presence/absence of the nerve stimulation by the nerve stimulator.

According to this aspect, when time intervals of the heartbeats detected by the heartbeat detector become short upon the occurrence of tachycardia or bradycardia of the heart, the nerve stimulator stimulate the nerve, thereby making it possible to lower the heart rate by suppressing the pulsing. In addition, by acquiring and processing the time-history information of the heartbeats stored in the storing unit, the state of the heart can be diagnosed for the period during which the time history of the heartbeats was stored.

In this case, the time history of the heartbeats is processed separating the heartbeats with the nerve stimulation and the heartbeats without the nerve stimulation. Accordingly, the unstimulated state of the heart of a patient is clearly ascertained from the time history of the heartbeats without the nerve stimulation, and the presence/absence of a therapeutic effect on the heart by the nerve stimulation and its extent are clearly ascertained from the time history of the heartbeats with the nerve stimulation, thereby making it possible to enhance the therapeutic effect on the heart.

In the above-described second aspect, the nerve stimulator may stimulate the nerve with different intensities on the basis of time intervals of the heartbeats detected by the heartbeat detector, and, in the case where the nerve stimulation is supplied, the storing unit stores the time history of the heartbeats in association with the intensities of the nerve stimulation.

By doing so, even when the nerve stimulation is performed while changing the intensity according to the state of the heart, it is possible to appropriately adjust the settings of individual intensities of the nerve stimulation by ascertaining the therapeutic effect of the nerve stimulation of the respective intensities.

In the above-described second aspect, the storing unit may be configured to store the nerve stimulation by the nerve stimulator in association with the heartbeats detected a predetermined delay time after the nerve stimulation.

By doing so, the nerve stimulation is associated with the heartbeat when the heart is actually responding to the nerve stimulation, thereby making it possible to more accurately ascertain the therapeutic effect of the nerve stimulation.

This configuration may be provided with a delay-time calculator that calculates the predetermined delay time on the basis of the length of the nerve from positions thereof to be stimulated by the nerve stimulator to the heart.

By doing so, the therapeutic effect of the nerve stimulation can be more accurately ascertained by more appropriately setting the delay time.

According to the first aspect of the embodiments of the present invention, an advantage is afforded in that the state of a heart can be accurately diagnosed even at the time of treatment by nerve stimulation, which can aid in appropriate treatment of the heart by nerve stimulation.

According to the second aspect of the embodiments of the present invention, an advantage is afforded in that the therapeutic effect on a heart by the nerve stimulation can be enhanced by clearly ascertaining its therapeutic effect.

What is claimed is:

1. A cardiac-event processor comprising:
a storing unit configured to store a time history of cardiac events, including heartbeats, in association with a presence/absence of nerve stimulation;
a heart rate calculator configured to calculate a heart rate for when each heartbeat is detected, on a basis of the time history of the cardiac events stored in the storing unit; and
a frequency data generator configured to separately add up frequencies of the heart rates calculated by the heart rate calculator for cases with and without the nerve stimulation,
wherein the presence of nerve stimulation is given as a tag to the time history, and
wherein the frequency data generator is configured to add up frequencies of the heart rates separately on the basis of existence or non-existence of the tags.

2. The cardiac-event processor according to claim 1, wherein the frequency data generator is configured to generate a histogram that shows a frequency distribution of the heart rates.

3. The cardiac-event processor according to claim 1, further comprising a display configured to separately display the frequencies of the heart rates with the nerve stimulation and the frequencies of the heart rates without the nerve stimulation, which are added up by the frequency data generator.

4. The cardiac-event processor according to claim 3, wherein
the frequency data generator is configured to add the frequencies of the heart rates with the nerve stimulation to the frequencies of the heart rates without the nerve stimulation to generate a histogram showing a frequency distribution of overall heart rates, and
the display is configured to display the histogram generated by the frequency data generator in such a way that the frequencies of the heart rates are displayed with different display appearances for cases with and without the nerve stimulation.

5. The cardiac-event processor according to claim 1, wherein the frequency data generator is configured to add the frequencies of the heart rates with the nerve stimulation to the frequencies of the heart rates without the nerve stimulation, and normalizes the frequencies of the heart rates with the nerve stimulation and the frequencies of the heart rates without the nerve stimulation by dividing them by the sum of the frequencies.

6. The cardiac-event processor according to claim 1, wherein,
in a case where the nerve stimulation is supplied, the storing unit is configured to store the time history of the heartbeats in association with an intensity of the nerve stimulation, and
the frequency data generator is configured to add up the frequencies of the heart rates with the nerve stimulation by sorting them according to a magnitude of the intensities of the nerve stimulation.

7. The cardiac-event processor according to claim 1, wherein, in the case where the nerve stimulation is supplied, the storing unit is configured to store the nerve stimulation in association with a heartbeat detected after a predetermined delay time from the nerve stimulation.

* * * * *